(12) United States Patent
Baynham et al.

(10) Patent No.: US 8,123,811 B2
(45) Date of Patent: Feb. 28, 2012

(54) CERVICAL IMPLANT

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 1205 days.

(21) Appl. No.: 11/741,265

(22) Filed: Apr. 27, 2007

(65) Prior Publication Data

US 2008/0269902 A1 Oct. 30, 2008

(51) Int. Cl.
*A61F 2/44* (2006.01)

(52) U.S. Cl. .................... 623/17.16; 606/246

(58) Field of Classification Search ..... 623/17.11–17.16
See application file for complete search history.

(56) References Cited

U.S. PATENT DOCUMENTS

| | | | |
|---|---|---|---|
| 5,607,424 A * | 3/1997 | Tropiano | 623/17.16 |
| 6,015,436 A | 1/2000 | Schonhoffer | |
| 6,090,143 A * | 7/2000 | Meriwether et al. | 623/17.11 |
| 6,120,506 A | 9/2000 | Kohrs et al. | |
| 6,245,108 B1 * | 6/2001 | Biscup | 623/17.11 |
| 6,562,074 B2 | 5/2003 | Gerbec et al. | |
| 6,666,889 B1 * | 12/2003 | Commarmond | 623/17.11 |
| 6,942,697 B2 * | 9/2005 | Lange et al. | 623/17.11 |
| 7,135,043 B2 * | 11/2006 | Nakahara et al. | 623/17.11 |
| 7,169,183 B2 * | 1/2007 | Liu et al. | 623/17.16 |
| 7,591,852 B2 * | 9/2009 | Prosser | 623/17.16 |
| 7,871,441 B2 * | 1/2011 | Eckman | 623/17.11 |
| 2003/0060886 A1 * | 3/2003 | Van Hoeck et al. | 623/17.11 |
| 2004/0122518 A1 | 6/2004 | Rhoda | |
| 2004/0176853 A1 * | 9/2004 | Sennett et al. | 623/17.16 |
| 2004/0186570 A1 | 9/2004 | Rapp | |
| 2005/0234556 A1 * | 10/2005 | Kretschmer | 623/17.15 |
| 2006/0167549 A1 * | 7/2006 | Mathys et al. | 623/17.11 |
| 2008/0154377 A1 * | 6/2008 | Voellmicke | 623/17.16 |
| 2008/0172128 A1 * | 7/2008 | Perez-Cruet et al. | 623/17.16 |

* cited by examiner

*Primary Examiner* — Eduardo C Robert
*Assistant Examiner* — Jerry Cumberledge
(74) *Attorney, Agent, or Firm* — McHale & Slavin, P.A.

(57) ABSTRACT

A spinal implant for insertion between adjacent vertebrae for promoting fusion of the vertebrae is a wedge shaped body with upper and lower plates separated by pyramidal sides with one large end and one small end enclosing the body. The upper and lower plates have elongated openings oriented perpendicularly to each other to form an internal labyrinth. The upper and lower openings are to be filled with thin layers of bone graft material to promote rapid ingrowth of living tissue.

5 Claims, 3 Drawing Sheets

CERVICAL IMPLANT

BACKGROUND OF THE INVENTION

1. Field of the Invention

This invention is in the field of orthopedics and, more particularly, directed to spinal implants.

2. Prior Art

Spinal stabilization is one approach to alleviating chronic back pain caused by displaced disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition, or in place of, the bone graft material, a spinal implant may be inserted in the intervertebral space.

The conventional surgical approach for stabilization has been posteriorly for ease of access to the spine and to avoid interfering with internal organs and tissue. Usually the implant site is prepared to maintain natural lordosis and to accept a certain sized implant within certain pressure limits. This requires considerable time and skill by the surgeon.

Published U. S. Patent Application, US 2004/0122518 A1, to Rhoda discloses a hollow wedge shaped vertebral implant used in fusing two adjacent vertebrae.

Published U.S. Patent Application, US 2004/0186570 A1, to Rapp discloses a intervertebral implant with upper and lower plates spaced apart by a wedge shaped strut. The plates are open and filled with bone graft material.

U.S. Pat. No. 6,562,074 to Gerber et al issued May 13, 2003 discloses a spinal insert which can be manipulated to adjust the height of the implant through links connected to the upper and lower plates.

U.S. Pat. No. 6,120,506 issued Sep. 19, 2000 to Kohrs et al discloses a lordotic implant and a tap for use in preparing the vertebrae. The implant is designed to be inserted between the non-parallel end plates of adjacent vertebrae and maintain the natural lordotic angle of the spine. This is done through the use of a threaded tapered plug inserted in a tapped hole in the direction required by the lordosis of the spine. The implant is hollow and has radial apertures for accommodating bone graft material.

U.S. Pat. No. 6,015,436 issued Jan. 18, 2000 to Shoenhoeffer discloses a tubular spinal implant. The implant is hollow and has radial apertures for interbody fusion through bone growth material. The device is placed between adjacent vertebrae with the opposite ends of the tube contacting the opposing vertebrae. The opposite ends are threaded together to form the hollow tube.

The prior art devices that incorporate bone graft material provide a solid plug of graft material contacting each adjacent vertebrae at the ends of the plug. A significant amount of time is required for the solid plug to become integrated with spiny ingrowth from the vertebrae.

Therefore, what is needed is an implant that provides quicker fusion and increased reinforcement between the end plates of the adjacent vertebrae.

SUMMARY OF THE PRESENT INVENTION

Disclosed is a spinal implant for insertion between adjacent vertebrae for promoting fusion of the vertebrae. The spinal implant has a wedge shaped body with upper and lower plates separated by pyramidal sides with one large end and one small end enclosing the body. The upper and lower plates have elongated openings oriented perpendicularly to each other to form an internal labyrinth. The upper and lower openings are to be filled with thin layers of bone graft material to promote rapid ingrowth of living tissue.

It is an objective of this invention to provide a spinal implant for maintaining the natural curvature of the spine and a interior labyrinth for ingrowth.

It is another objective of this invention to provide a cervical implant with reinforcement between the end plates.

It is a further objective of this invention to provide a one piece cervical implant with retainer elements at each of the corners for anchoring the implant to the bone.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
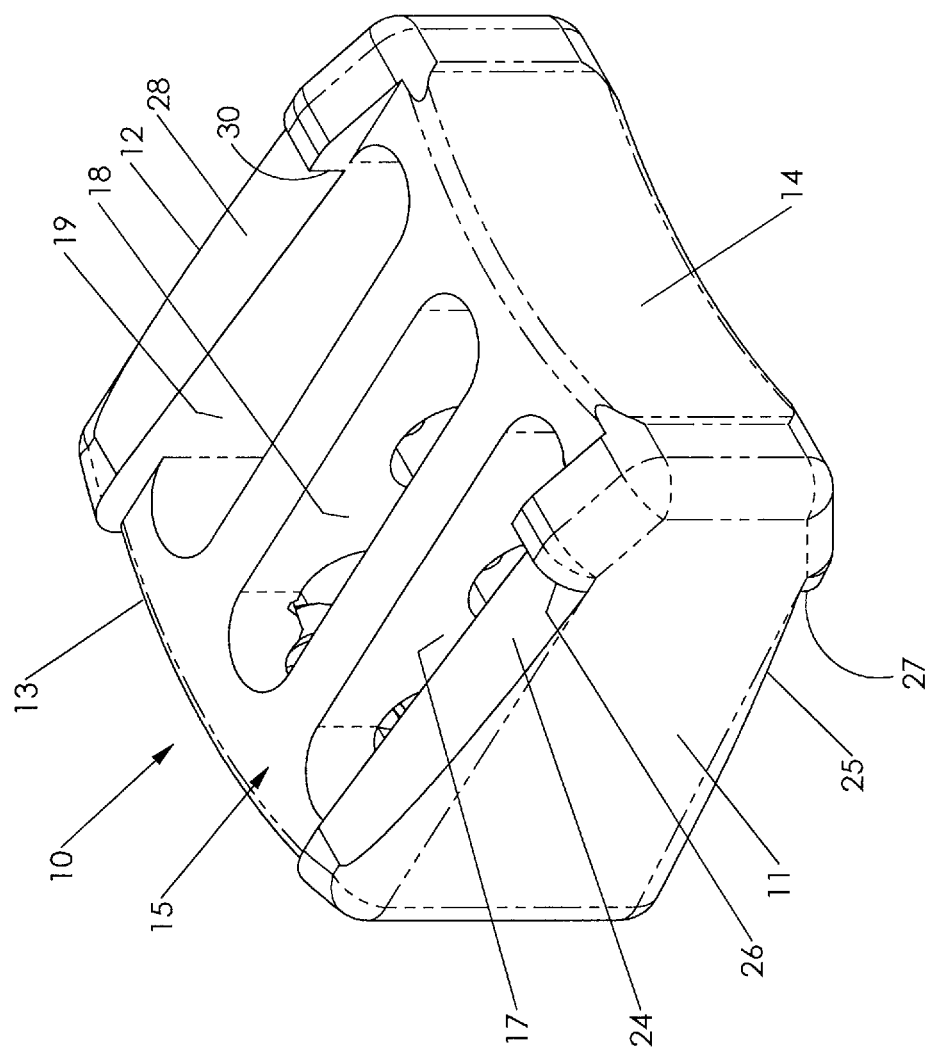
FIG. 1 is a perspective of the spinal implant of this invention.
Figure 2:
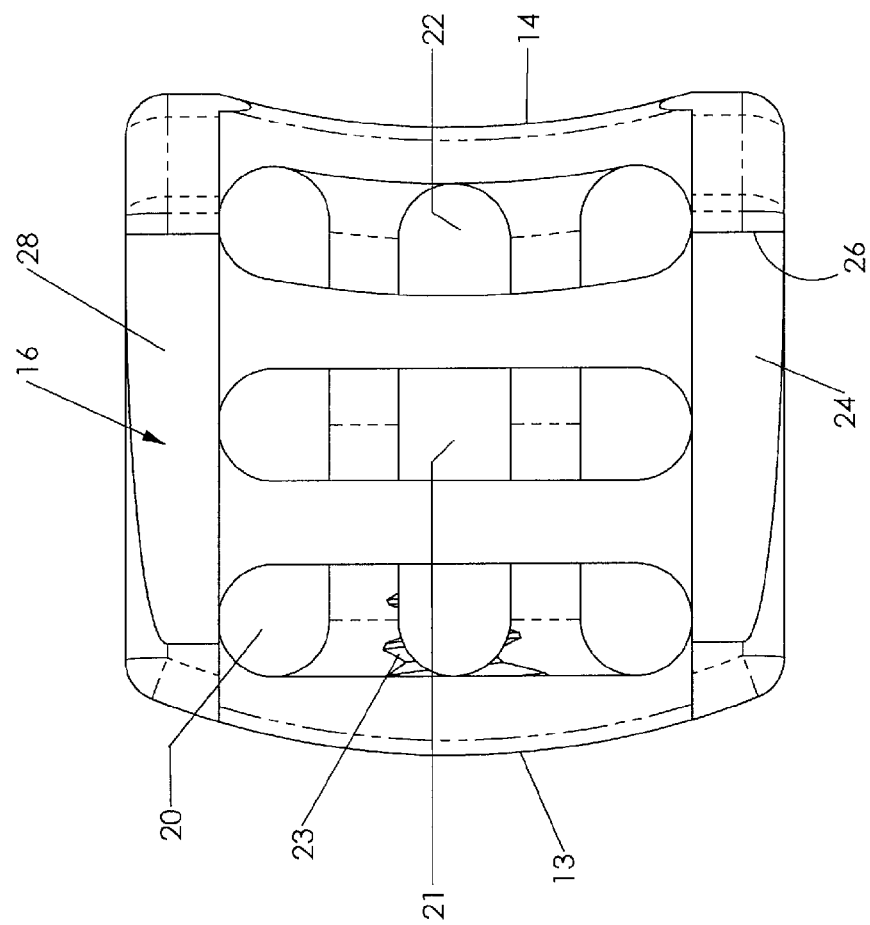
FIG. 2 is plan view of one end plate.
Figure 3:
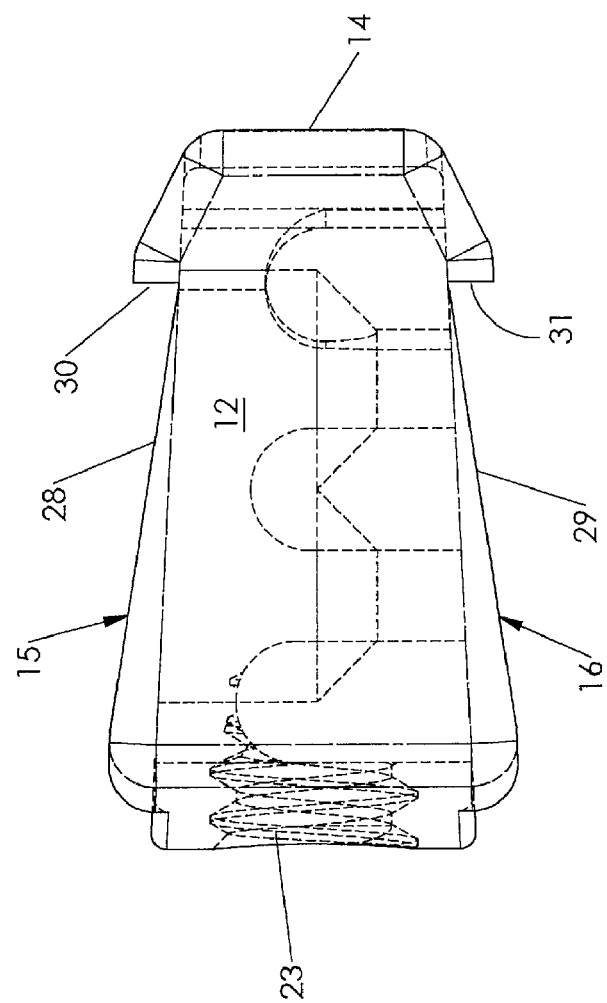
FIG. 3 is a side view of the spinal implant of this invention.

The cervical implant 10 has truncated pyramidal sides 11 and 12 joined with a larger rectilinear curved end 13 and a smaller curved end 14 forming an over-all wedge shaped body with rounded corners. A retainer cleat extends outwardly from each of the corners. Larger end 13 is convexly curved outwardly from the body and smaller end 14 is concavely curved toward the body. The major surfaces form end plates 15 and 16 which are rectilinear with curved ends. The body may be machined or otherwise fabricated as a unitary, monolithic implant.

The end plates 15 and 16 will be in contact with the end plates of adjacent vertebrae when the body is implanted in the spine of the patient. The implantation site will be prepared by removing the damaged intervertebral disk tissue. The vertebral end plates will be shaved to insure a vascularized bed for the implant and the rapid ingrowth of living tissue into and through the implant to fuse the adjacent vertebrae. To increase the development of spinal ingrowth, the end plate 15 has a series of longitudinal openings 17, 18 and 19 extending from the area of the larger end 13 toward the smaller end 14. The end plate 16 has a series of elongated openings 20, 21 and 22 extending across the width of the plate perpendicularly to the openings 17, 18 and 19. These two series of openings interconnect approximately half way between the end plate 15 and end plate 16 to create a labyrinth of open space within the implant.

Larger end 13 has a threaded bore 23 which is used to connect the implant with instrumentation facilitating the placement of the implant in the prepared surgical site. Also, pyramidal side 11 has planar grooves 24 and 25 defined by end walls 26 and 27 of the retainers, respectively. Pyramidal side wall 12 includes planar grooves 28 and 29 defined by end walls 30 and 31 of the retainers, respectively. These planar grooves and end walls cooperate with instrumentation used in implanting the device. The instrumentation (not shown), when in place, extends from the large curved end toward the smaller curved end and engages the end walls to place the implant in the proper position.

Before implantation, a thin layer of bone or bone growth promoting material or a combination thereof, is placed in the longitudinal openings 17, 18 and 19 to fill those openings. Another thin layer of bone or bone growth promoting material is placed in the openings 20, 21 and 22. These layers contact each other near the center of the implant. In this manner, the boney ingrowth is promoted by increasing the number of surfaces available for vascularization and by directing the growth from end plate to end plate by channeling the growth through the openings.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A cervical implant for fusion of adjacent vertebrae comprising a body having opposite major surfaces for contacting the end plates of adjacent vertebrae, respectively, said opposite major surfaces having opposite ends and opposite sides, respectively, one of said opposite major surfaces having a first series of openings therein, the other of said opposite major surfaces having a second series of openings therein, said first and second series of openings extending perpendicularly to each other, said first and said second series of openings communicate within said body forming a labyrinth, said opposite sides are pyramidal, respectively, resulting in a wedge shape with one large opposite end and one small opposite end, and retainers each including a planar groove and end wall extending outwardly from said small opposite end for anchoring said body, wherein corners are formed by said opposite ends joining said opposite major surfaces, respectively, said retainers extending outwardly from said major surfaces at said corners, said body being one piece and said openings filled with bone growth material.

2. The cervical implant of claim 1 wherein said first opposite end is convexly curved.

3. The cervical implant of claim 1 wherein said second opposite end is concavely curved.

4. The cervical implant of claim 3 wherein said first opposite end is convexly curved.

5. The cervical implant of claim 1 wherein said opposite ends joining said opposite major surfaces, respectively, said first series of openings extending from said first opposite end toward said second opposite end, said second series of openings extending perpendicularly to said first series of openings.

* * * * *